US010709439B2

(12) United States Patent
Malkowski

(10) Patent No.: US 10,709,439 B2
(45) Date of Patent: Jul. 14, 2020

(54) ENDOSCOPIC STITCHING DEVICE

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

(*) Notice: Subject to any disclaimer, the term of this patent is extended or adjusted under 35 U.S.C. 154(b) by 355 days.

(21) Appl. No.: 15/866,811

(22) Filed: Jan. 10, 2018

(65) Prior Publication Data

US 2018/0221011 A1 Aug. 9, 2018

Related U.S. Application Data

(60) Provisional application No. 62/455,119, filed on Feb. 6, 2017.

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0625* (2013.01); *A61B 17/06166* (2013.01);
(Continued)

(58) Field of Classification Search
CPC . A61B 17/04; A61B 17/0469; A61B 17/0491; A61B 17/06; A61B 17/06166;
(Continued)

(56) References Cited

U.S. PATENT DOCUMENTS 1,822,330 A 9/1931 Ainslie
2,327,353 A 8/1943 Karle
(Continued)

FOREIGN PATENT DOCUMENTS

EP 0 647 431 A2 4/1995
WO 9811829 A1 3/1998
(Continued)

OTHER PUBLICATIONS

Partial European Search Report issued in European Appln. No. 18155068.2 dated Jun. 11, 2018.
Extended European Search Report issued in Application No. 18155068.2, dated Jun. 28, 2019.

*Primary Examiner* — Robert A Lynch
(74) *Attorney, Agent, or Firm* — Carter, DeLuca & Farrell LLP

(57) ABSTRACT

An endoscopic stitching device includes a handle assembly having a main rod and first and second blade control members, and an elongate shaft assembly having first and second blade drive members, an axial rod, and an end effector. The first and second blade drive members are received in respective first and second grooves of the first and second blade control members and rotated about the first and second blade control members to be secured with a circumferential groove of the first and second blade control members, such that the first and second blade control members are movable with the respective first and second blade drive members. The axial rod is detachably coupled with the main rod for concomitant movement therewith. The end effector includes jaws operatively coupled with the axial rod, and needle receiving blades operatively coupled with the respective first and second blade drive members.

20 Claims, 8 Drawing Sheets

(51) Int. Cl.
*A61B 17/06* (2006.01)
*A61B 17/00* (2006.01)
*A61B 17/12* (2006.01)
*A61B 17/29* (2006.01)
*A61B 17/34* (2006.01)

(52) U.S. Cl.
CPC ......... *A61B 17/12013* (2013.01); *A61B 17/29* (2013.01); *A61B 17/3417* (2013.01); *A61B 2017/0046* (2013.01); *A61B 2017/00477* (2013.01); *A61B 2017/0608* (2013.01); *A61B 2017/0609* (2013.01)

(58) Field of Classification Search
CPC .............. A61B 17/12013; A61B 17/29; A61B 17/3417; A61B 2017/0046; A61B 2017/0472
See application file for complete search history.

(56) References Cited

U.S. PATENT DOCUMENTS

| | | | |
|---|---|---|---|
| 3,073,311 A | 1/1963 | Tibbs et al. | |
| 3,123,077 A | 3/1964 | Alcamo | |
| 4,236,470 A | 12/1980 | Stenson | |
| 5,037,433 A | 8/1991 | Wilk et al. | |
| 5,042,707 A | 8/1991 | Taheri | |
| 5,100,430 A | 3/1992 | Avellanet et al. | |
| 5,209,747 A | 5/1993 | Knoepfler | |
| 5,300,082 A | 4/1994 | Sharpe et al. | |
| 5,308,353 A | 5/1994 | Beurrier | |
| 5,314,445 A | 5/1994 | Heidmueller nee Degwitz et al. | |
| 5,330,502 A | 7/1994 | Hassler et al. | |
| 5,350,391 A | 9/1994 | Iacovelli | |
| 5,374,277 A | 12/1994 | Hassler | |
| 5,389,103 A | 2/1995 | Melzer et al. | |
| 5,403,342 A | 4/1995 | Tovey et al. | |
| 5,439,478 A | 8/1995 | Palmer | |
| 5,454,823 A | 10/1995 | Richardson et al. | |
| 5,454,827 A | 10/1995 | Aust et al. | |
| 5,480,406 A | 1/1996 | Nolan et al. | |
| 5,540,706 A | 7/1996 | Aust et al. | |
| 5,562,686 A | 10/1996 | Sauer et al. | |
| 5,564,615 A | 10/1996 | Bishop et al. | |
| 5,575,799 A | 11/1996 | Bolanos et al. | |
| 5,582,617 A | 12/1996 | Klieman et al. | |
| 5,591,181 A | 1/1997 | Stone et al. | |
| 5,601,224 A | 2/1997 | Bishop et al. | |
| 5,620,415 A | 4/1997 | Lucey et al. | |
| 5,643,294 A | 7/1997 | Tovey et al. | |
| 5,674,229 A | 10/1997 | Tovey et al. | |
| 5,690,652 A | 11/1997 | Wurster et al. | |
| 5,690,653 A | 11/1997 | Richardson et al. | |
| 5,752,973 A | 5/1998 | Kieturakis | |
| 5,759,188 A | 6/1998 | Yoon | |
| 5,766,196 A | 6/1998 | Griffiths | |
| 5,779,646 A | 7/1998 | Koblish et al. | |
| 5,792,165 A | 8/1998 | Klieman et al. | |
| 5,797,537 A | 8/1998 | Oberlin et al. | |
| 5,797,927 A | 8/1998 | Yoon | |
| 5,814,054 A | 9/1998 | Kortenbach et al. | |
| 5,817,119 A | 10/1998 | Klieman et al. | |
| 5,827,323 A | 10/1998 | Klieman et al. | |
| 5,865,836 A | 2/1999 | Miller | |
| 5,871,488 A | 2/1999 | Tovey et al. | |
| 5,876,412 A | 3/1999 | Piraka | |
| 5,897,563 A | 4/1999 | Yoon et al. | |
| 5,906,630 A | 5/1999 | Anderhub et al. | |
| 5,908,428 A | 6/1999 | Scirica et al. | |
| 5,928,136 A | 7/1999 | Barry | |
| 5,931,855 A | 8/1999 | Buncke | |
| 5,954,731 A | 9/1999 | Yoon | |
| 5,954,733 A | 9/1999 | Yoon | |
| 5,957,937 A | 9/1999 | Yoon | |
| 5,984,932 A | 11/1999 | Yoon | |
| 5,993,466 A | 11/1999 | Yoon | |
| 5,993,467 A | 11/1999 | Yoon | |
| 5,997,565 A | 12/1999 | Inoue | |
| 6,004,332 A | 12/1999 | Yoon et al. | |
| 6,017,358 A | 1/2000 | Yoon et al. | |
| 6,027,522 A | 2/2000 | Palmer | |
| 6,077,287 A | 6/2000 | Taylor et al. | |
| 6,080,180 A | 6/2000 | Yoon et al. | |
| 6,086,601 A | 7/2000 | Yoon | |
| 6,126,665 A | 10/2000 | Yoon | |
| 6,139,563 A | 10/2000 | Cosgrove, III et al. | |
| 6,143,005 A | 11/2000 | Yoon et al. | |
| 6,171,316 B1 | 1/2001 | Kovac et al. | |
| 6,206,893 B1 | 3/2001 | Klein et al. | |
| 6,214,028 B1 | 4/2001 | Yoon et al. | |
| 6,223,100 B1 | 4/2001 | Green | |
| 6,224,614 B1 | 5/2001 | Yoon | |
| 6,261,307 B1 | 7/2001 | Yoon et al. | |
| 6,319,262 B1 | 11/2001 | Bates et al. | |
| 6,358,259 B1 | 3/2002 | Swain et al. | |
| 6,494,888 B1 | 12/2002 | Laufer et al. | |
| 6,506,196 B1 | 1/2003 | Laufer | |
| 6,517,539 B1 | 2/2003 | Smith et al. | |
| 6,569,105 B1 | 5/2003 | Kortenbach et al. | |
| 6,582,450 B2 | 6/2003 | Ouchi | |
| 6,638,287 B2 | 10/2003 | Danitz et al. | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,676,676 B2 | 1/2004 | Danitz et al. | |
| 6,743,239 B1 | 6/2004 | Kuehn et al. | |
| 6,743,240 B2 | 6/2004 | Smith et al. | |
| 6,755,843 B2 | 6/2004 | Chung | |
| 6,773,441 B1 | 8/2004 | Laufer et al. | |
| 6,821,285 B2 | 11/2004 | Laufer et al. | |
| 6,835,200 B2 | 12/2004 | Laufer et al. | |
| 6,889,116 B2 | 5/2005 | Jinno | |
| 6,936,061 B2 | 8/2005 | Sasaki | |
| 6,972,017 B2 | 12/2005 | Smith et al. | |
| 6,981,628 B2 | 1/2006 | Wales | |
| 6,997,931 B2 | 2/2006 | Sauer et al. | |
| 7,052,489 B2 | 5/2006 | Griego et al. | |
| RE39,152 E | 6/2006 | Aust et al. | |
| 7,063,715 B2 | 6/2006 | Onuki et al. | |
| 7,107,124 B2 | 9/2006 | Green | |
| 7,153,314 B2 | 12/2006 | Laufer et al. | |
| 7,248,944 B2 | 7/2007 | Green | |
| 8,628,545 B2 | 1/2014 | Cabrera et al. | |
| 9,271,723 B2 | 3/2016 | Taylor et al. | |
| 2004/0010245 A1 | 1/2004 | Cerier et al. | |
| 2004/0060409 A1 | 4/2004 | Leung et al. | |
| 2004/0060410 A1 | 4/2004 | Leung et al. | |
| 2005/0096694 A1 | 5/2005 | Lee | |
| 2005/0256533 A1 | 11/2005 | Roth et al. | |
| 2006/0069396 A1 | 3/2006 | Meade et al. | |
| 2006/0111732 A1 | 5/2006 | Gibbens et al. | |
| 2006/0253126 A1 | 11/2006 | Bjerken et al. | |
| 2006/0282093 A1 | 12/2006 | Shelton et al. | |
| 2007/0005110 A1 | 1/2007 | Collier et al. | |
| 2008/0045976 A1 | 2/2008 | Gibbons et al. | |
| 2009/0259233 A1 | 10/2009 | Bogart et al. | |
| 2009/0312773 A1* | 12/2009 | Cabrera ........... A61B 17/00234 606/144 |
| 2013/0158568 A1 | 6/2013 | Kia et al. | |
| 2016/0345958 A1 | 12/2016 | Martin et al. | |
| 2016/0367243 A1 | 12/2016 | Martin et al. | |

FOREIGN PATENT DOCUMENTS

| | | |
|---|---|---|
| WO | 0174254 A1 | 10/2001 |
| WO | 03017850 A2 | 3/2003 |
| WO | 03028541 A2 | 4/2003 |
| WO | 2006061868 A1 | 6/2006 |
| WO | 2009/132284 A2 | 10/2009 |
| WO | 2015095133 A1 | 6/2015 |

* cited by examiner

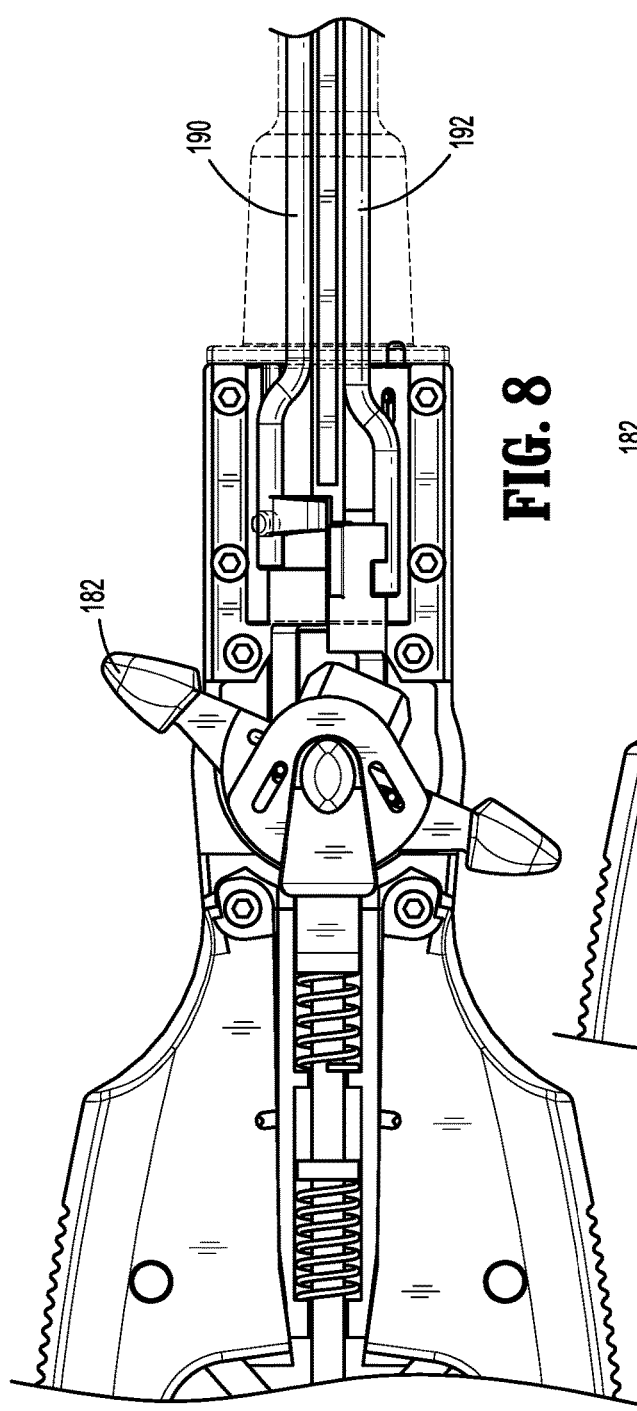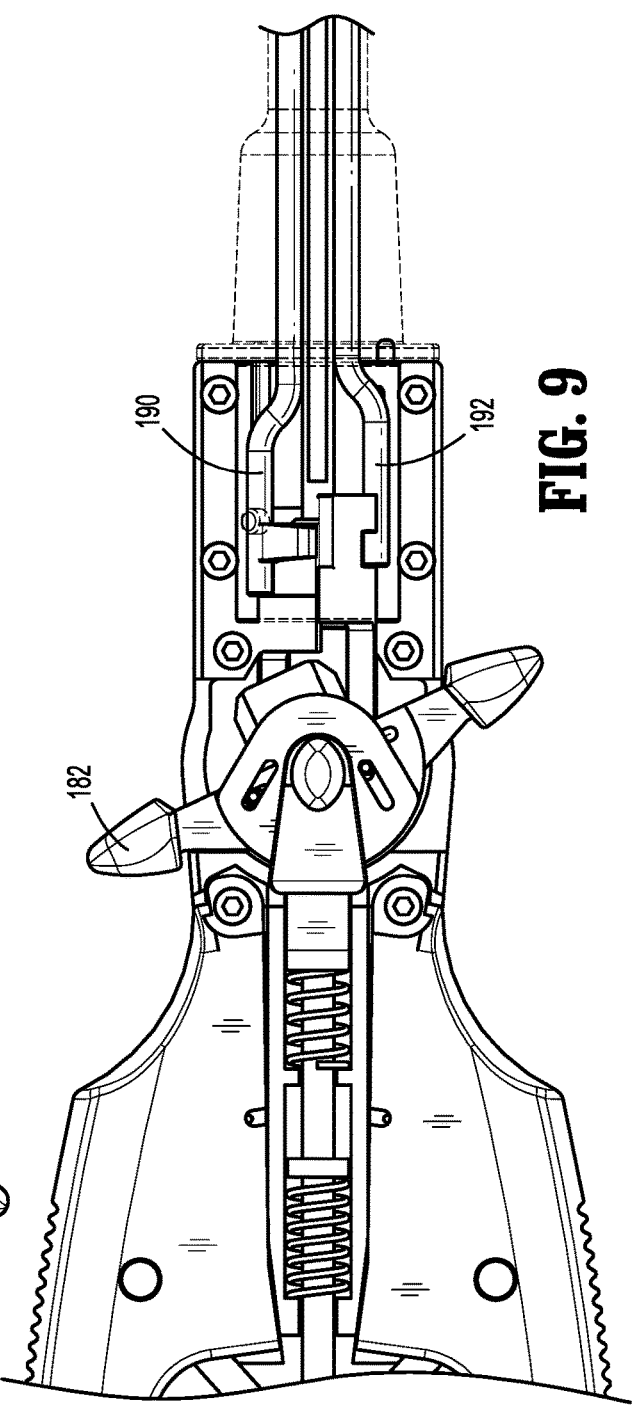

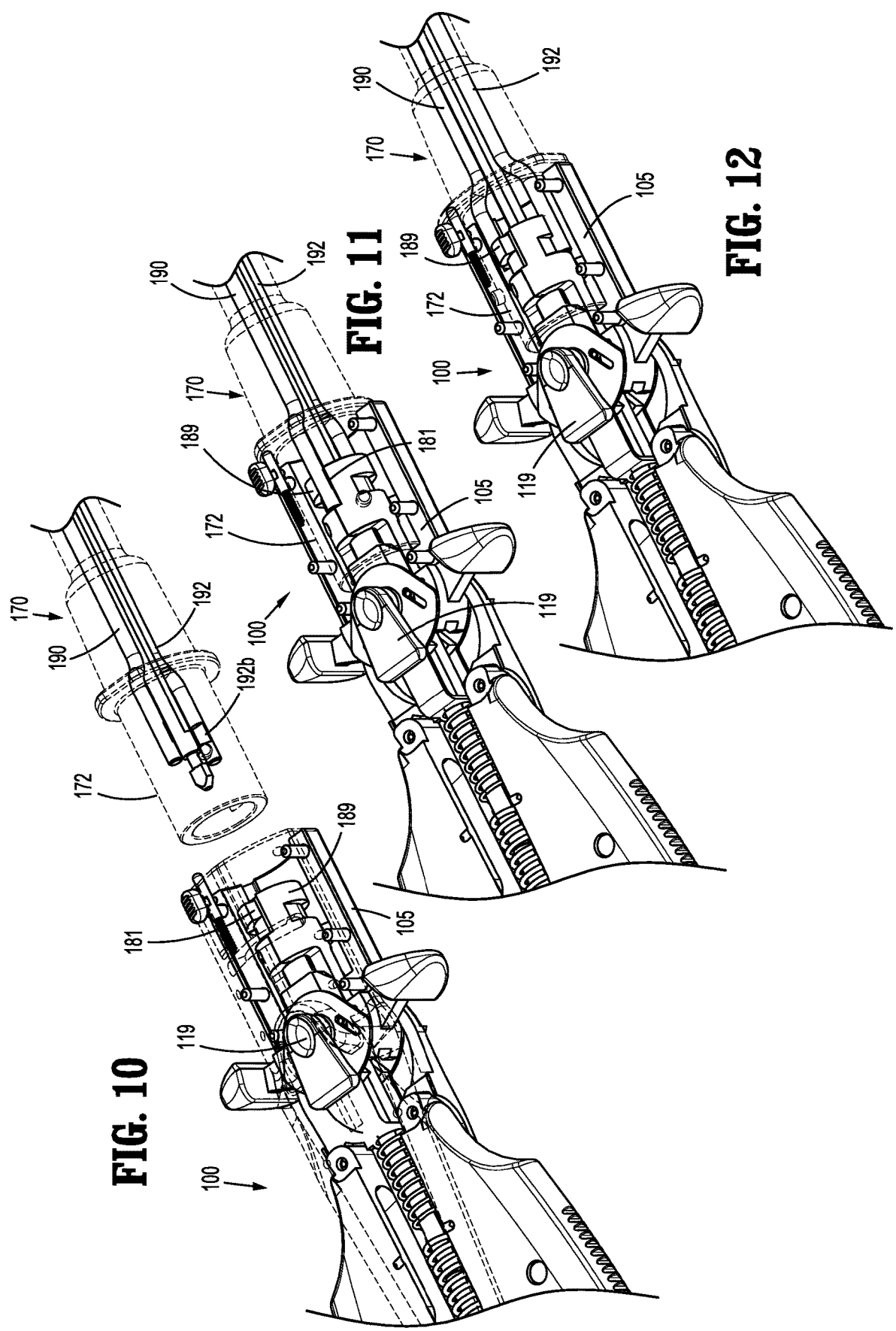

ENDOSCOPIC STITCHING DEVICE

CROSS-REFERENCE TO RELATED APPLICATION

This application claims the benefit of and priority to U.S. Provisional Patent Application No. 62/455,119 filed Feb. 6, 2017, the entire disclosure of which is incorporated by reference herein.

BACKGROUND

Technical Field

The present disclosure relates to devices for suturing or stitching and, more particularly, to devices for endoscopic suturing and/or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. Suturing may be challenging during endoscopic surgery because of the small openings through which the suturing of bodily organs or tissues must be accomplished. Accordingly, a need exists for simple and effective devices for endoscopic suturing or stitching.

SUMMARY

The present disclosure describes a device for suturing and stitching that demonstrates a practical approach to meeting the performance requirements and overcoming usability challenges associated with endoscopic suturing or stitching. In accordance with an embodiment of the present disclosure, there is provided an endoscopic stitching device including a handle assembly and an elongate shaft assembly.

The handle assembly includes a main rod configured for axial displacement and first and second blade control members movable relative to each other. The first and second blade control members define first and second longitudinal grooves and a circumferential groove.

The elongate shaft assembly is detachably coupled with the handle assembly. The elongate shaft assembly includes first and second blade drive members, an axial rod, and an end effector. The first and second blade drive members are received in the respective first and second longitudinal grooves of the first and second blade control members and are rotated about the first and second blade control members to be secured with the circumferential groove of the first and second blade control members, such that the first and second blade control members are movable with the respective first and second blade drive members. The axial rod is detachably coupled with the main rod for concomitant movement therewith.

The end effector includes first and second jaws and first and second needle receiving blades. The first and second jaws are operatively coupled with the axial rod, whereby axial displacement of the main rod pivots the first and second jaws between open and closed positions. The first and second needle receiving blades are slidably disposed in the respective first and second jaws. The first and second needle receiving blades are operatively coupled with the respective first and second blade drive members, whereby reciprocating axial displacement of the first and second blade control members causes reciprocating axial displacement of the first and second needle receiving blades.

In an embodiment, the first and second blade control members, when in a neutral position, may define a cylindrical profile. The first and second blade control members may define a bore configured to receive the main rod therethrough.

In another embodiment, the main rod may include a distal end defining a cavity configured to engage a proximal end of the axial rod. The cavity of the main rod may have a non-circular cross-section to engage the proximal end of the axial rod in a selective orientation.

In yet another embodiment, a proximal portion of each of the first and second blade drive members may include a cutout configured to rotatably receive a proximal flange defined by the circumferential groove of the first and second blade control members.

In still another embodiment, the first and second longitudinal grooves of the first and second blade control members may diametrically oppose each other.

In still yet another embodiment, the circumferential groove of the first and second blade control members may be partially defined around a circumference of the first and second blade control members to limit rotation of the first and second blade drive members about the first and second blade control members. The first and second blade drive members may be rotatable about 90 degrees from the respective first and second longitudinal grooves of the first and second blade control members.

In accordance with another embodiment of the present disclosure, there is provided an endoscopic stitching device including a handle assembly and an elongate shaft assembly. The handle assembly includes a main rod and first and second blade control members movable relative to each other. The elongate shaft assembly is detachably coupled with the handle assembly. The elongate shaft assembly includes first and second blade drive members, an axial rod, and an end effector. The first and second blade drive members are operatively engagable with the respective first and second blade control members. The elongate shaft assembly is transitionable between a neutral position in which the first and second blade control members are movable independent of the first and second blade drive members and an engaged position in which the first and second blade control members are movable with the respective first and second blade drive members. The axial rod is detachably coupled with the main rod for concomitant movement therewith. The end effector includes first and second jaws and first and second needle receiving blades. The first and second jaws are operatively coupled with the axial rod, whereby axial displacement of the main rod pivots the first and second jaws between open and closed positions. The first and second needle receiving blades are slidably disposed in the respective first and second jaws. The first and second needle receiving blades are operatively coupled with the respective first and second blade drive members, whereby reciprocating axial displacement of the first and second blade control members causes reciprocating axial displacement of the first and second needle receiving blades.

In an embodiment, the elongate shaft assembly may be rotatable relative to the handle assembly to transition the elongate shaft assembly between the neutral position and the engaged position.

In another embodiment, the first and second blade control members may define a cylindrical profile in a neutral state. The first and second blade control members may define a bore configured to receive the main rod therethrough. In addition, at least a portion of the main rod of the handle assembly may be interposed between the first and second blade control members.

In yet another embodiment, a distal end portion of the main rod may be configured to engage a proximal end of the axial rod in a selective orientation.

In still yet another embodiment, the first and second blade control members may define grooves configured to receive respective first and second blade drive members in the neutral position. The grooves of the first and second blade control members may diametrically oppose each other. In addition, the first and second blade control members may further define a circumferential groove configured to rotatably receive proximal portions of the first and second blade drive members. In an embodiment, the circumferential groove of the first and second blade control members may be defined partially around a circumference of the first and second blade control members to limit rotation of the first and second blade drive members about the first and second blade control members.

In still yet another embodiment, the handle assembly may further include a button configured to transition the first and second blade control members between a reload mode in which the first and second blade control members are in a distal-most position and a suturing mode in which the first and second blade control members are in a proximal position.

DETAILED DESCRIPTION OF THE DRAWINGS

The foregoing objects, features and advantages of the disclosure will become more apparent from a reading of the following description in connection with the accompanying drawings, in which:

FIGS. 8 and 9 are partial, top views of the handle assembly of FIG. 1, illustrating use of a toggle mechanism of the handle assembly; and FIGS. 10-12 are partial perspective views of the stitching device of FIG. 1, illustrating attachment of the elongate shaft assembly to the handle assembly.

DETAILED DESCRIPTION

Figure 1:
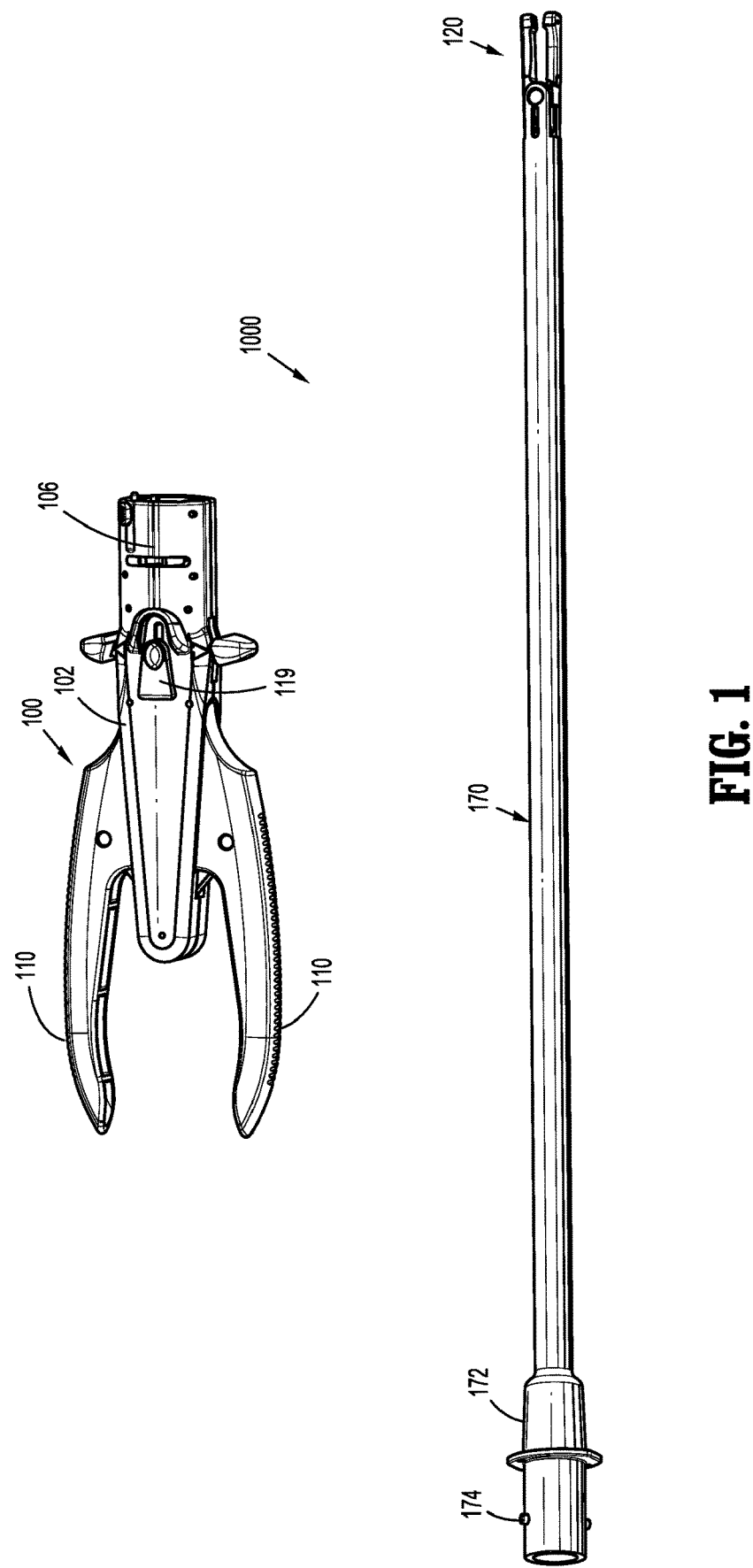
FIG. 1 is a perspective view of a stitching device in accordance with an embodiment of the present disclosure, illustrating a handle assembly detached from an elongate shaft assembly.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, an embodiment of the present disclosure is generally shown as a stitching device 1000. Stitching device 1000 is adapted to be particularly useful in endoscopic or laparascopic procedures, wherein an endoscopic portion of stitching device 1000 such as, e.g., a tool assembly 200, is insertable into an operative site, via a cannula assembly or the like (not shown). Stitching device 1000 includes a handle assembly 100 and an elongate shaft assembly 170 extending distally from handle assembly 100. Handle assembly 100 and elongate shaft assembly 170 may be detachably coupled, as will be described hereinbelow. Such a configuration facilitates, e.g., sterilization of stitching device 1000.

Figure 2:
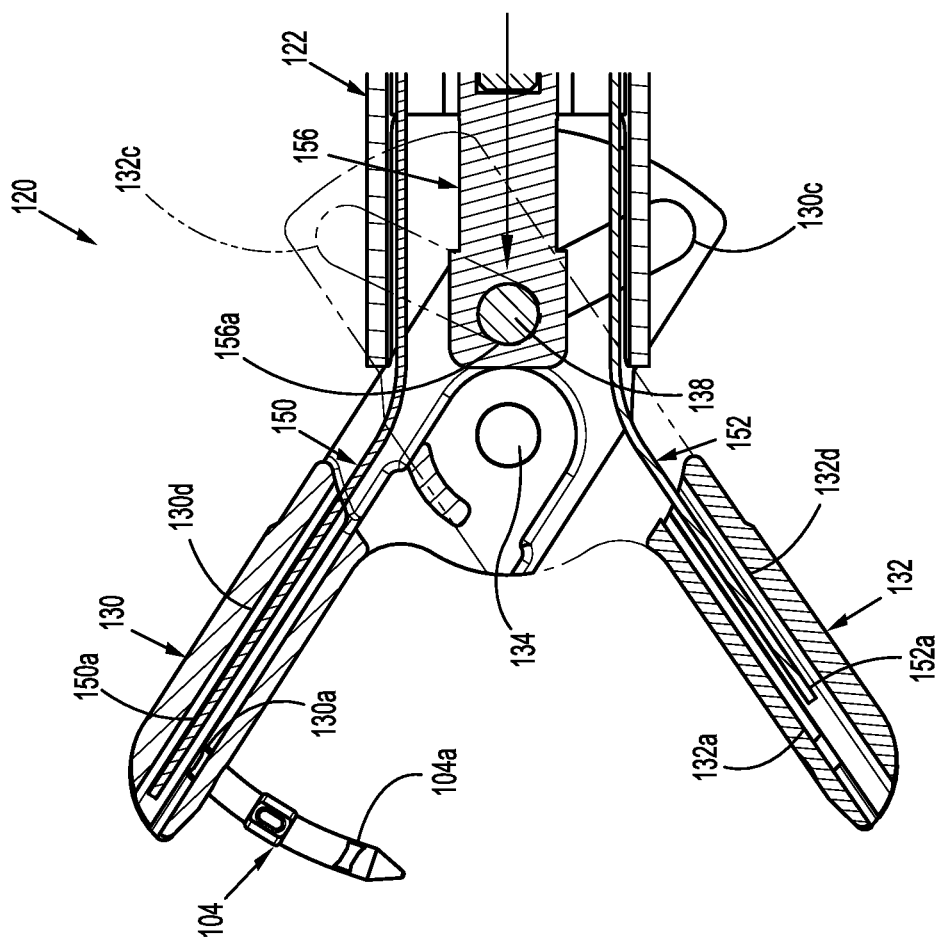
FIG. 2 is a partial cross-sectional view of a tool assembly of the elongate shaft assembly of FIG. 1.

With reference to FIGS. 1 and 2, elongate shaft assembly 170 includes a tool assembly 120. Tool assembly 120 includes a support member 122 and jaws 130, 132 pivotably mounted on support member 122 by means of a jaw pivot pin 134. To move jaws 130, 132 between an open position and a closed position, an axial rod 156 has a camming pin 138 mounted at a distal end 156a thereof. Camming pin 138 rides in angled camming slots 130c, 132c defined in respective jaws 130, 132 such that axial or longitudinal movement of axial rod 156 causes jaws 130, 132 to be cammed between the open and closed positions.

Tool assembly 120 further includes a pair of needle engaging members or blades 150, 152 which are slidably supported within support member 122. Each blade 150, 152 includes a distal end 150a, 152a slidably extending into blade receiving channels 130d, 132d of respective jaws 130, 132. Channels 130d, 132d are dimensioned to at least partially intersect needle recesses 130a, 132a. Thus, by advancing blade 150 or 152 within respective channel 130d, 132d, distal end 150a, 152a of advancing blade 150, 152 engages or "locks in" a groove 104a formed in needle 104 when at least a portion of needle 104 is received within respective recesses 130a, 132a. A suture (not shown) may be secured to needle 104. The suture may include a plurality of barbs oriented to resist movement in a direction opposite to the direction of travel.

Figure 3:
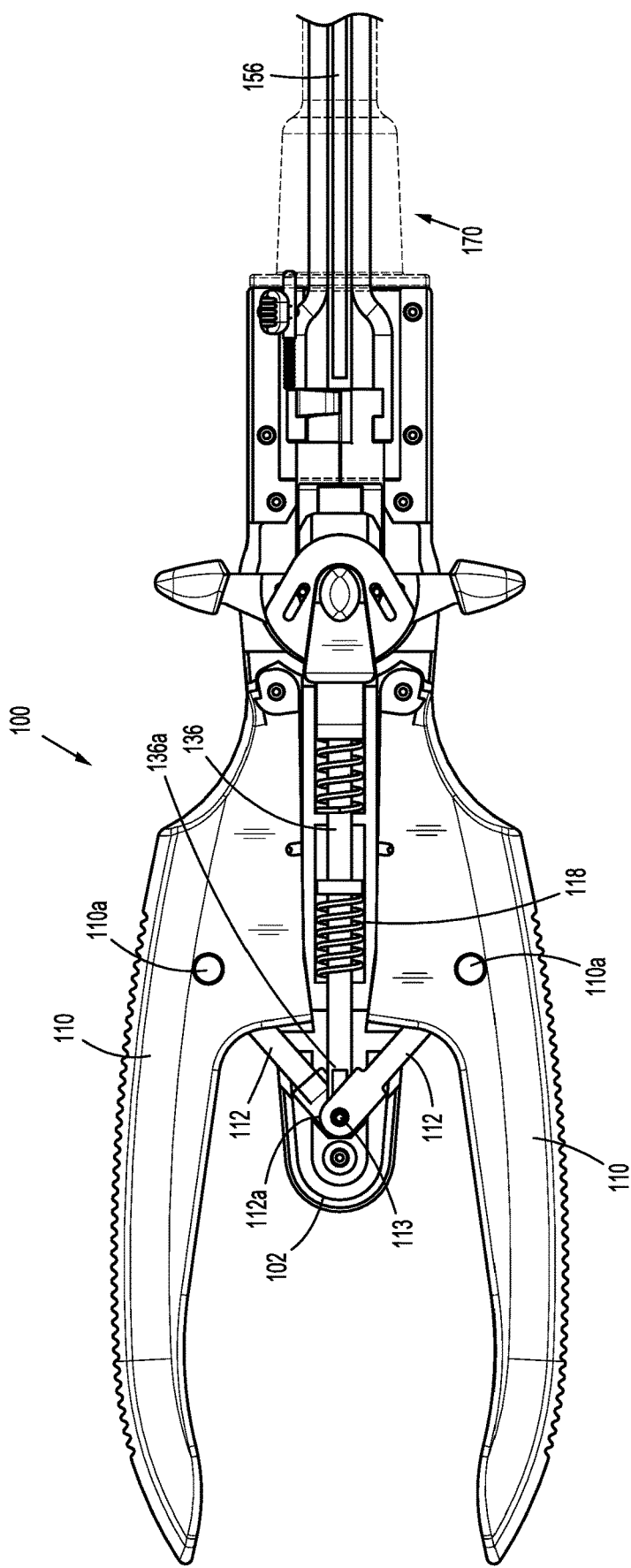
FIG. 3 is a partial top view of the handle assembly of FIG. 1 with a top half of a housing removed, illustrating a needle loading/retaining assembly.

With reference now to FIG. 3, handle assembly 100 includes a pair of handles 110 pivotably secured to housing 102. Handles 110 are operatively coupled by link members 112. Each link member 112 has a first end (not shown) pivotably connected to respective handles 110 at a pivot point 110a and a second end 112a pivotally connected to a proximal portion 136a of main rod 136 by a pin 113. Under such a configuration, when handles 110 are squeezed, link members 112 advance main rod 136 proximally. Main rod 136 may be provided with, e.g., biasing members 118, in the form of a return spring, to bias main rod 136 to the initial position. Main rod 136 is detachably coupled to an axial rod 156 of elongate shaft assembly 170. When handles 110 are squeezed, main rod 136 is displaced proximally, which, in turn, causes axial displacement of axial rod 156. Axial rod 156 is operatively coupled to jaws 130, 132 (FIG. 2) of tool assembly 120, such that axial displacement of axial rod 156 transitions jaws 130, 132 between the open and closed positions.

Figure 4:
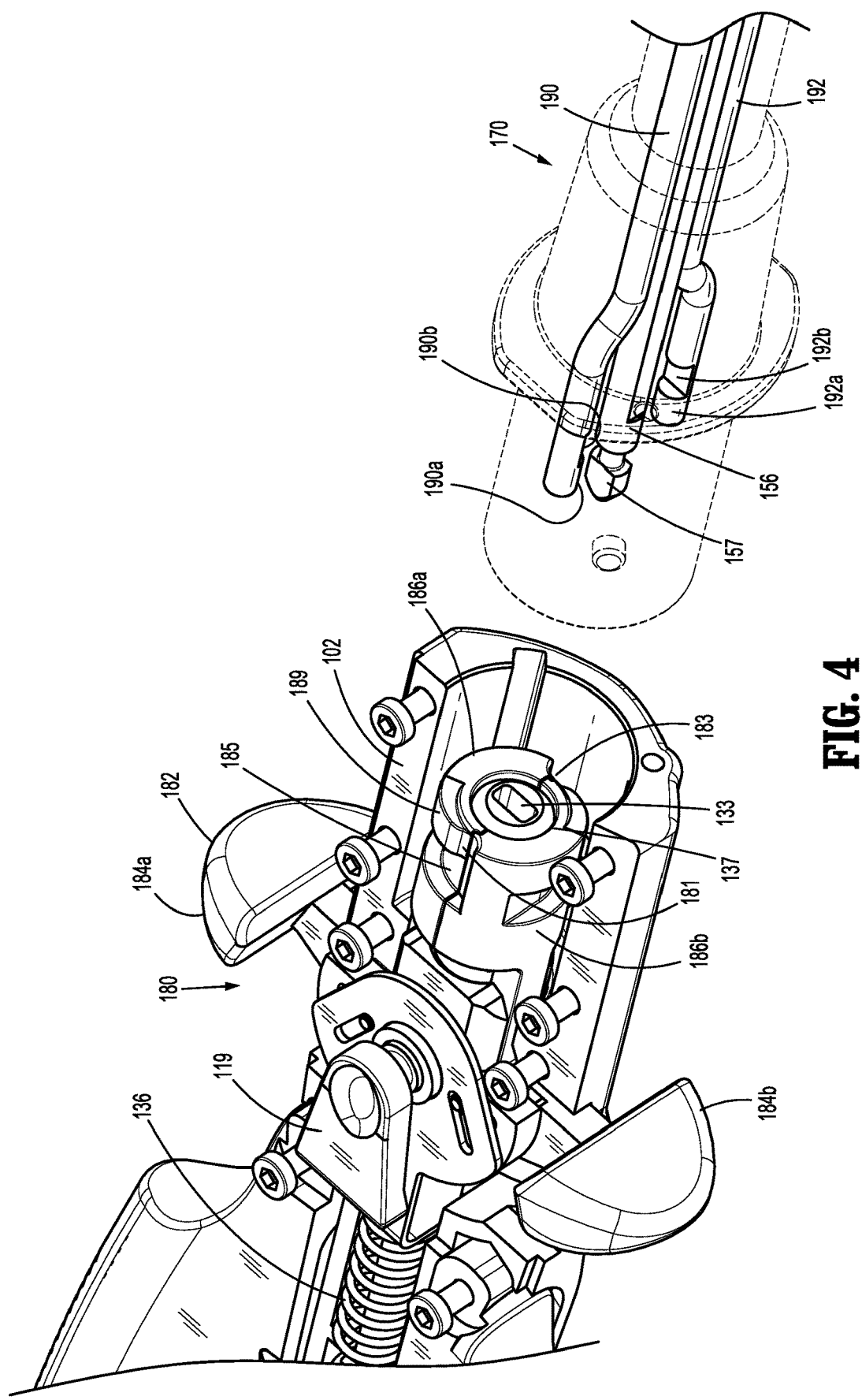
FIG. 4 is a partially enlarged perspective view of the handle assembly of FIG. 1 with the top half of the housing removed, illustrating the elongate shaft assembly detached from the handle assembly.
Figure 5:
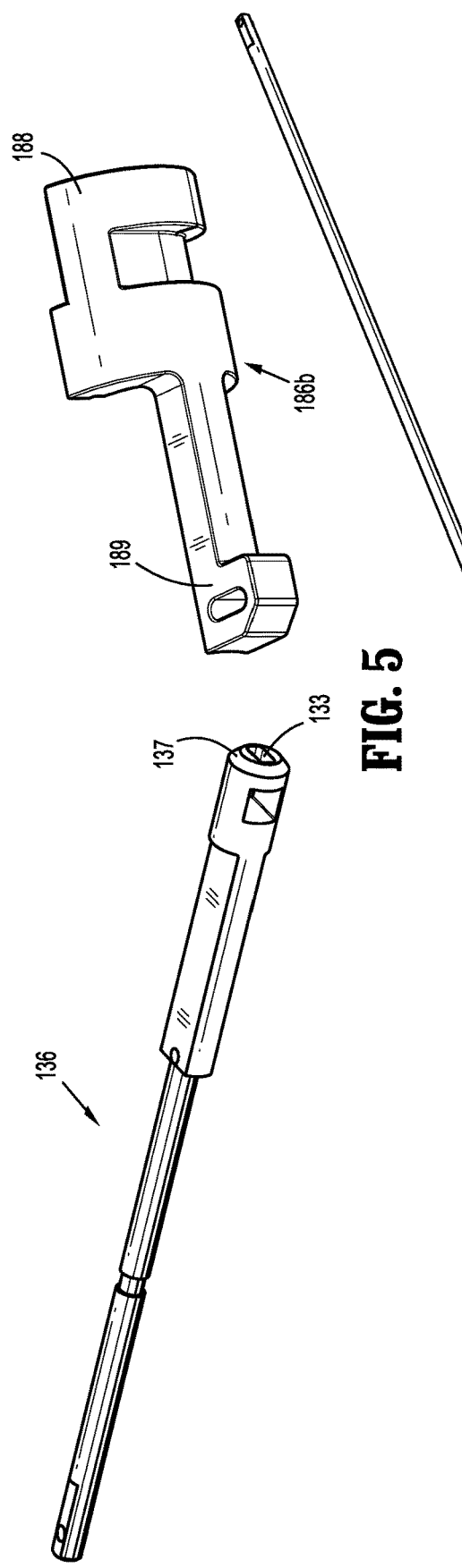
FIG. 5 is a perspective view of a blade control member and a main rod of the handle assembly of FIG. 1.

With reference now to FIGS. 4 and 5, handle assembly 100 further includes a needle loading/retaining assembly 180. Needle loading/retaining assembly 180 includes a toggle 182 pivotally supported in housing 102 and having a pair of arms 184a, 184b extending transversely from housing 102. Needle loading/retaining assembly 180 further includes a first blade control member 186a and a second blade control member 186b. Each of first and second blade control members 186a, 186b includes a proximal end (not shown) connected to respective arms 184a, 184b of toggle 182. As toggle 182 is pivoted in a first direction, first blade control member 186a is moved in a first direction and second blade control member 186b is moved in a second direction opposite to the first direction, and vice-versa. Reference may be made to U.S. Pat. No. 8,628,545, entitled "Endoscopic Stitching Devices," the entire content of which is incorporated herein by reference, for a detailed discussed of the construction and operation of a handle assembly and an end effector.

With continued reference now to FIGS. 4 and 5, a distal end of each blade control member 186a, 186b is detachably connected to respective first and second blade drive members 190, 192. First and second blade control members 186a, 186b each include a body 188 and a finger 189 extending proximally from body 188. Fingers 189 are coupled to respective arms 184a, 184b of toggle 182 such that when toggle 182 is pivoted, first and second blade control members 186a, 186b move relative to each other, which, in turn, provides reciprocating axial displacement of first and second blade drive members 190, 192. When first and second blade control members 186a, 186b are in a neutral state (FIG. 4), respective bodies 188 of first and second blade control members 186a, 186b define a cylindrical profile opening dimensioned to receive main rod 136 therein.

First and second blade control members 186a, 186b define first and second longitudinal grooves 181, 183. Each of first and second longitudinal grooves 181, 183 extends along a length of bodies 188 of respective first and second blade control members 186a, 186b such that first and second longitudinal grooves 181, 183 are configured to receive at least a portion of respective first and second blade drive members 190 192. In particular, first and second longitudinal grooves 181, 183 may diametrically oppose each other.

In addition, first and second blade control members 186a, 186b each define a circumferential groove 185 dimensioned to rotatably receive a least a portion of proximal portion 190a, 192a of respective first and second blade drive members 190, 192. Circumferential grooves 185 are defined around a portion of the circumference of first and second blade drive members 190, 192 to limit rotation of elongate shaft assembly 170 about first and second blade drive members 190, 192. For example, rotation of elongate shaft assembly 170 about first and second blade drive members 190, 192 may be limited to about 90 degrees.

Proximal portions 190a, 192a of respective first and second blade drive members 190, 192 define respective cutouts 190b, 192b. Cutouts 190b, 192b are dimensioned to receive a circumferential flange 189 of first and second blade control members 186a, 186b. Proximal portion 190a, 192a of first and second blade drive members 190, 192 serve as locking members dimensioned to be rotatably received in circumferential grooves 185 of first and second blade control members 186a, 186b.

In addition, handle assembly 100 further includes a button 119 (FIG. 1), operatively coupled with needle loading/retaining assembly 180, to slide needle loading/retaining assembly 180 distally to transition handle assembly 100 to a reload mode. In the reload mode, first and second blade control members 186a, 186b are in a distal position such that both blades 150, 152 (FIG. 2) are in a distal-most position. In this manner, notches (not shown) formed in respective blades 150, 152 are aligned with or in registration with respective needle receiving openings (not shown) defined in respective jaws 130, 132. With the notches of blades 150, 152 aligned with or in registration with the respective needle receiving openings of respective jaws 130, 132, needle 104 (FIG. 2) may be positioned or loaded into a selected one needle receiving opening of jaws 130, 132.

Figure 6:
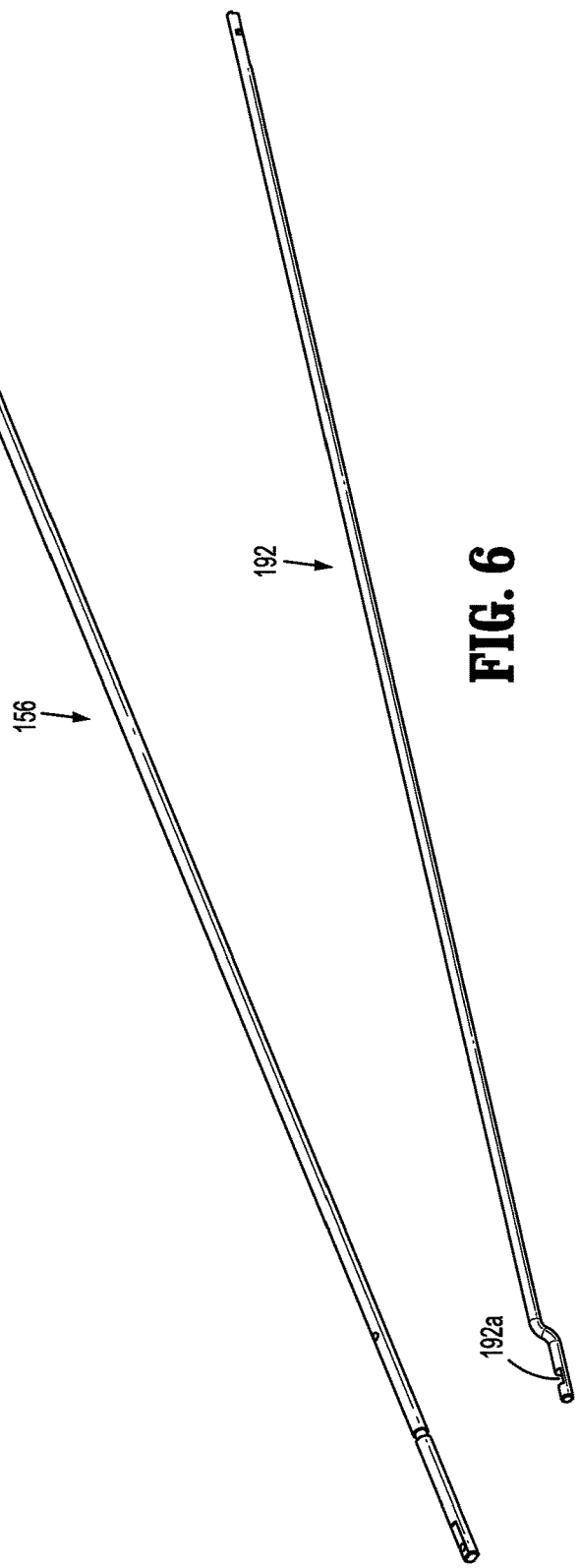
FIG. 6 is a perspective view of an axial rod and a blade drive member of the elongate shaft assembly of FIG. 1.
Figure 7:
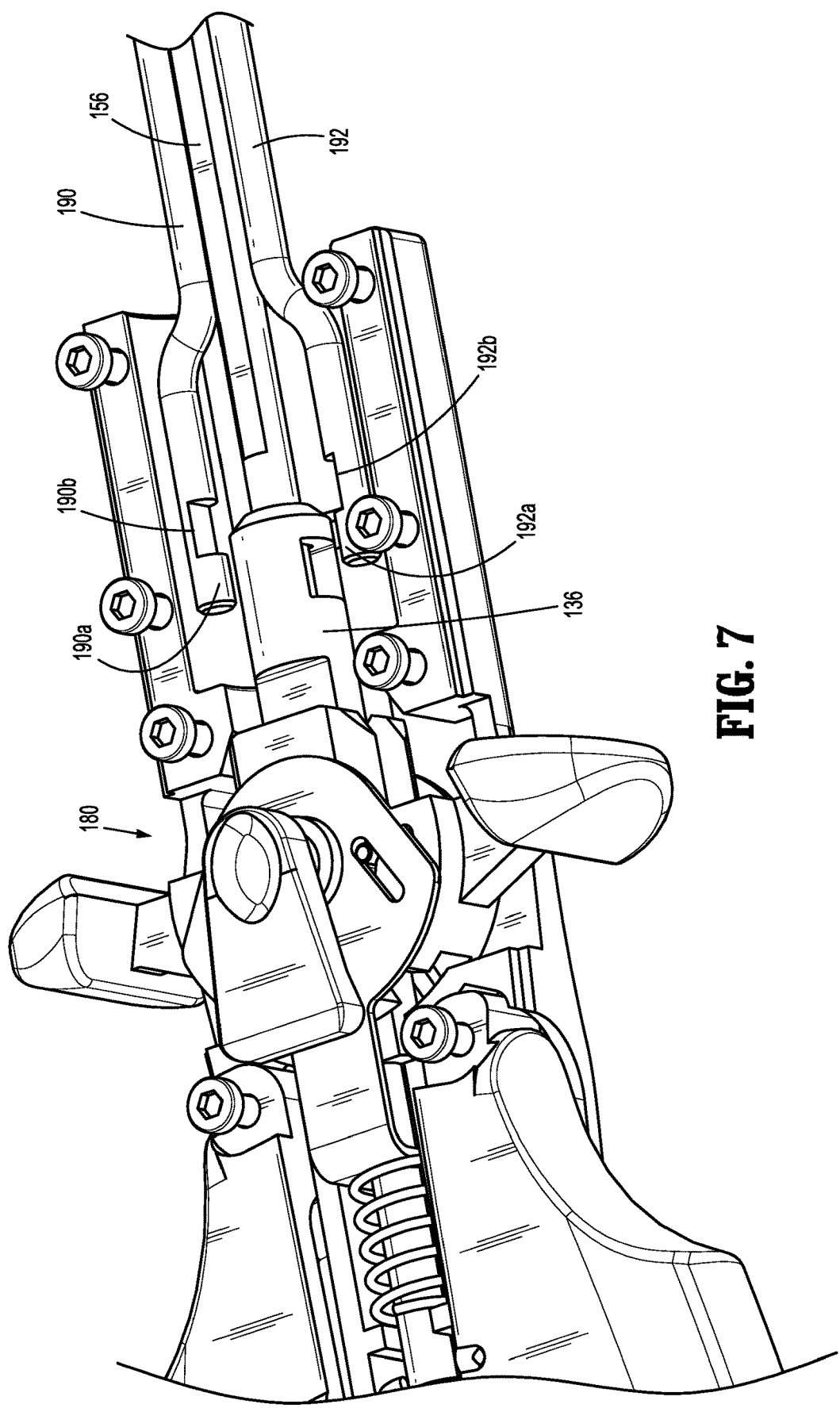
FIG. 7 is a partially enlarged perspective view of the handle assembly of FIG. 4 with an elongate shaft of the elongate shaft assembly removed, illustrating attachment of the elongate shaft assembly with the handle assembly.

With reference to FIGS. 4-6, a distal end 137 of main rod 136 defines a cavity 133 configured to receive a proximal end 157 of axial rod 156. Cavity 133 may include a non-circular cross-section complementary to a cross-section of axial rod 156 to receive axial rod 156 in a selective orientation. For example, cavity 133 of main rod 136 may have a rectangular cross-section to align first and second blade drive members 190, 192 with respective first and second longitudinal grooves 181, 183. Once first and second blade drive members 190, 192 are received in first and second longitudinal grooves 181, 183, elongate shaft assembly 170 may be rotated, e.g., about 90 degrees clockwise (FIG. 7), about a longitudinal axis of elongate shaft assembly 170 such that at least a portion of circumferential flange 189 is rotatably received in cutouts 190b, 192b of first and second blade drive members 190, 192 and, respective proximal portion 190a, 192a of first and second blade drive members 190, 192 are rotatably received in circumferential grooves 185 of first and second blade controls 186a, 186b. In this manner, first and second blade drive members 190, 192 are operatively coupled with respective first and second blade control members 186a, 186b.

With reference to FIGS. 8 and 9, toggle 182 may be pivoted to cause reciprocating axial displacement of first and second blade drive members 190, 192 to provide axial displacement of blades 150, 152 (FIG. 2) of tool assembly 120 to enable swapping of needle 104 between jaws 130, 132.

With reference to FIGS. 10-12, initially, handle assembly 100 and elongate shaft assembly 170 are detached. A proximal portion 172 of elongate shaft assembly 170 is inserted into a hub 105 of handle assembly 100. It is envisioned that, e.g., a boss 174 (FIG. 1), may be provided on proximal portion 172 of elongate shaft assembly 170, and housing 102 may be provided with indicia or a complementary slot 106 to receive boss 174 in order to further facilitate alignment of elongate shaft assembly 170 with handle assembly 100. Once first and second blade drive members 190, 192 are received in first and second longitudinal grooves 181, 183 (FIG. 4), elongate shaft assembly 170 may be rotated, e.g., clockwise, about a longitudinal axis of elongate shaft assembly 170 such that circumferential flange 189 (FIG. 4) is rotatably received in cutouts 190b, 192b (FIG. 4) of first and second blade drive members 190, 192, and respective proximal portions 190a, 192a (FIG. 7) of first and second blade drive members 190, 192 are received in circumferential grooves 185 (FIG. 4) of first and second blade controls members 186a, 186b. However, when first and second blade drive members 190, 192 are received in first and second longitudinal grooves 181 prior to the rotation of elongate shaft assembly 170, first and second blade control members 186a, 186b may be movable independent of first and second blade drive members 190, 192. In this manner, first and second blade drive members 190, 192 are detachably coupled with respective first and second blade control members 186a, 186b for concomitant axial displacement.

In use, when stitching device 1000 is transitioned to the reload mode by pushing button 119 (FIG. 1), first and second blade control members 186a, 186b are in a distal position such that both blades 150, 152 (FIG. 2) are in a distal-most position. In this manner, notches (not shown) formed in respective blades 150, 152 are aligned with or in registration with respective needle receiving openings (not shown) defined in respective jaws 130, 132. With the notches of blades 150, 152 aligned with or in registration with the respective needle receiving openings of respective jaws 130, 132, needle 104 (FIG. 2) may be positioned or loaded into a selected one needle receiving opening of jaws 130, 132.

Once needle 104 is loaded into one of the needle receiving openings of jaws 130, 132, main rod 136 is moved in a proximal direction to thereby cause each blade 150, 152 to engage a respective groove 104a of needle 104. With needle 104 engaged by both blades 150, 152, toggle 182 is actuated or rotated so that only one blade 150, 152, is in engagement with needle 104 (FIG. 2), and the other blade 150, 152 is disengaged from needle 104. With only one blade 150, 152 engaged with needle 104, handles 110 may be released, thereby moving main rod 136 distally to open jaws 130, 132.

With jaws 130, 132 in the open position and needle 104 loaded and held in one jaw 130 or 132, jaws 130, 132 may be positioned about or over a target tissue and handles 110 may be actuated to approximate jaws 130, 132. As jaws 130, 132 are approximated, the exposed end of needle 104 is penetrated through the target tissue and enters opposed jaw 130 or 132. With needle 104 in opposed jaw 130 or 132, toggle 182 is once again actuated or rotated so that blades 150, 152 are reversed. In so doing, needle 104 is swapped from one blade 150 or 152 to the other blade 150 or 152, and thus, loaded or held in the other jaw 130 or 132.

With needle 104 being swapped from one blade 150, 152 to another blade 150, 152, handles 110 may be released to thereby open jaws 130, 132 and draw needle 104 through the target tissue. In so doing, suture 106 is also drawn through the tissue. The process is repeated, passing needle 104 between jaws 130, 132 and drawing the suture through the target tissue, thereby suturing the target tissue as needed or desired.

The detachability of elongate shaft assembly 170 with handle assembly 100 without sacrificing operability of stitching device 1000 enhances reusability of stitching device 1000 by facilitating, e.g., sterilization of stitching device 1000. In addition, the detachability of elongate shaft assembly 170 enables use with a plurality of elongate shaft assemblies 170 having various lengths to meet the needs of each surgical procedure.

Although the illustrative embodiments of the present disclosure have been described herein with reference to the accompanying drawings, the above description, disclosure, and figures should not be construed as limiting, but merely as exemplifications of particular embodiments. For example, elongate shaft assembly 170 may include an articulable section to facilitate maneuverability of stitching device through the anatomical structure of the patient. It is to be understood, therefore, that the disclosure is not limited to those precise embodiments, and that various other changes and modifications may be effected therein by one skilled in the art without departing from the scope or spirit of the disclosure.

What is claimed is:

1. An endoscopic stitching device, comprising:
    a handle assembly including:
        a main rod configured for axial displacement; and
        first and second blade control members movable relative to each other, the first and second blade control members defining first and second longitudinal grooves and a circumferential groove; and
    an elongate shaft assembly detachably coupled with the handle assembly, the elongate shaft assembly including:
        first and second blade drive members received in the respective first and second longitudinal grooves of the first and second blade control members and rotated about the first and second blade control members to be secured with the circumferential groove of the first and second blade control members, such that the first and second blade control members are movable with the respective first and second blade drive members;
    an axial rod detachably coupled with the main rod for concomitant movement therewith; and
    an end effector including:
        first and second jaws operatively coupled with the axial rod, whereby axial displacement of the main rod pivots the first and second jaws between open and closed positions; and
        first and second needle receiving blades slidably disposed in the respective first and second jaws, the first and second needle receiving blades operatively coupled with the respective first and second blade drive members, whereby reciprocating axial displacement of the first and second blade control members causes reciprocating axial displacement of the first and second needle receiving blades.

2. The endoscopic stitching device according to claim 1, wherein the first and second blade control members, when in a neutral position, define a cylindrical profile.

3. The endoscopic stitching device according to claim 1, wherein the first and second blade control members define a bore configured to receive the main rod therethrough.

4. The endoscopic stitching device according to claim 1, wherein the main rod includes a distal end defining a cavity configured to engage a proximal end of the axial rod.

5. The endoscopic stitching device according to claim 4, wherein the cavity of the main rod has a non-circular cross-section to engage the proximal end of the axial rod in a selective orientation.

6. The endoscopic stitching device according to claim 1, wherein a proximal portion of each of the first and second blade drive members includes a cutout configured to rotatably receive a proximal flange defined by the circumferential groove of the first and second blade control members.

7. The endoscopic stitching device according to claim 1, wherein the first and second longitudinal grooves of the first and second blade control members diametrically oppose each other.

8. The endoscopic stitching device according to claim 1, wherein the circumferential groove of the first and second blade control members is partially defined around a circumference of the first and second blade control members to limit rotation of the first and second blade drive members about the first and second blade control members.

9. The endoscopic stitching device according to claim 8, wherein the first and second blade drive members are rotatable about 90 degrees from the respective first and second longitudinal grooves of the first and second blade control members.

10. An endoscopic stitching device, comprising:
a handle assembly including:
a main rod; and
first and second blade control members movable relative to each other; and
an elongate shaft assembly detachably coupled with the handle assembly, the elongate shaft assembly including:
first and second blade drive members operatively engageable with the respective first and second blade control members, the elongate shaft assembly transitionable between a neutral position in which the first and second blade control members are movable independent of the first and second blade drive members and an engaged position in which the first and second blade control members are movable with the respective first and second blade drive members as a single construct;
an axial rod detachably coupled with the main rod for concomitant movement therewith; and
an end effector including:
first and second jaws operatively coupled with the axial rod, whereby axial displacement of the main rod pivots the first and second jaws between open and closed positions; and
first and second needle receiving blades slidably disposed in the respective first and second jaws, the first and second needle receiving blades operatively coupled with the respective first and second blade drive members, whereby reciprocating axial displacement of the first and second blade control members causes reciprocating axial displacement of the first and second needle receiving blades.

11. The endoscopic stitching device according to claim 10, wherein the elongate shaft assembly is rotatable relative to the handle assembly to transition the elongate shaft assembly between the neutral position and the engaged position.

12. The endoscopic stitching device according to claim 10, wherein the first and second blade control members define a cylindrical profile in a neutral state.

13. The endoscopic stitching device according to claim 12, wherein the first and second blade control members define a bore configured to receive the main rod therethrough.

14. The endoscopic stitching device according to claim 12, wherein at least a portion of the main rod of the handle assembly is interposed between the first and second blade control members.

15. The endoscopic stitching device according to claim 14, wherein a distal end portion of the main rod is configured to engage a proximal end of the axial rod in a selective orientation.

16. The endoscopic stitching device according to claim 12, wherein the first and second blade control members define grooves configured to receive the respective first and second blade drive members in the neutral position.

17. The endoscopic stitching device according to claim 16, wherein the grooves of the first and second blade control members diametrically oppose each other.

18. The endoscopic stitching device according to claim 12, wherein the first and second blade control members further define a circumferential groove configured to rotatably receive a proximal portion of the first and second blade drive members.

19. The endoscopic stitching device according to claim 18, wherein the circumferential groove of the first and second blade control members is defined partially around a circumference of the first and second blade control members to limit rotation of the first and second blade drive members about the first and second blade control members.

20. The endoscopic stitching device according to claim 10, wherein the handle assembly further includes a button configured to transition the first and second blade control members between a reload mode in which the first and second blade control members are in a distal-most position and a suturing mode in which the first and second blade control members are in a proximal position.

* * * * *